United States Patent
Quistgaard et al.

(10) Patent No.: US 6,962,566 B2
(45) Date of Patent: Nov. 8, 2005

(54) MEDICAL DIAGNOSTIC ULTRASOUND INSTRUMENT WITH ECG MODULE, AUTHORIZATION MECHANISM AND METHODS OF USE

(75) Inventors: Jens U. Quistgaard, Seattle, WA (US); Leo R. Catallo, Mercer Island, WA (US); Anthony R. Vannelli, Monroe, WA (US); Blake W. Little, Bothell, WA (US); Randy T. Holmberg, Bothell, WA (US); Juin Jet Hwang, Mercer Island, WA (US); Clinton T. Siedenburg, Marysville, WA (US); Ramchandra Pailoor, Woodinville, WA (US); D. Scott Hirschi, Snohomish, WA (US); Hung Nguyen, Everett, WA (US)

(73) Assignee: Sonosite, Inc., Bothwell, WA (US)

( * ) Notice: Subject to any disclaimer, the term of this patent is extended or adjusted under 35 U.S.C. 154(b) by 214 days.

(21) Appl. No.: 10/062,179

(22) Filed: Feb. 1, 2002

(65) Prior Publication Data

US 2003/0009102 A1 Jan. 9, 2003

Related U.S. Application Data

(63) Continuation-in-part of application No. 09/840,002, filed on Apr. 19, 2001, now Pat. No. 6,569,101.

(51) Int. Cl.[7] .............................. A61B 8/00; A61B 5/04
(52) U.S. Cl. ....................................... 600/437; 600/513
(58) Field of Search ................................. 600/437, 439, 600/443, 453–456, 509–513

(56) References Cited

U.S. PATENT DOCUMENTS

| | | | |
|---|---|---|---|
| 4,649,930 A | * 3/1987 | Groch et al. | 600/508 |
| 5,427,111 A | * 6/1995 | Traub et al. | 600/508 |
| 5,634,465 A | * 6/1997 | Schmiesing et al. | 600/454 |
| 5,647,366 A | 7/1997 | Weng | |
| 5,722,412 A | 3/1998 | Pflugrath et al. | |
| 5,839,442 A | 11/1998 | Chiang et al. | |
| 5,893,363 A | 4/1999 | Little et al. | |
| 5,935,074 A | 8/1999 | Mo et al. | |
| 6,048,319 A | 4/2000 | Hudgins et al. | |
| 6,126,608 A | 10/2000 | Kemme et al. | |
| 6,203,498 B1 | 3/2001 | Bunce et al. | |
| 6,248,073 B1 | 6/2001 | Gilbert | |
| 6,251,073 B1 | 6/2001 | Imran et al. | |
| 6,416,475 B1 | 7/2002 | Hwang et al. | |
| 6,561,979 B1 | * 5/2003 | Wood et al. | 600/437 |
| 6,569,101 B2 | * 5/2003 | Quistgaard et al. | 600/459 |

* cited by examiner

Primary Examiner—Francis J. Jaworski
(74) Attorney, Agent, or Firm—Fulbright & Jaworski LLP

(57) ABSTRACT

A handheld ultrasound instrument is disclosed having enhanced diagnostic modes including pulse/continuous wave Doppler, time-motion analysis, spectral analysis and tissue harmonic imaging. An external electrocardiograph (ECG) recording unit is also disclosed. The ECG unit is adaptable to be used with the handheld ultrasound instrument to provide for ECG monitoring while performing an ultrasound scan in B-mode, Doppler, color Doppler, M-mode, and CW/PW mode. The enhanced handheld ultrasound instrument further includes a security mechanism allowing any combination of the diagnostic modes to be enabled by the manufacturer, and later to enable or disable any one or group of the diagnostic modes. The invention also discloses a method for a manufacturer to maintain a database of handheld ultrasound instrument capabilities after the instruments enter the stream of commerce.

15 Claims, 13 Drawing Sheets

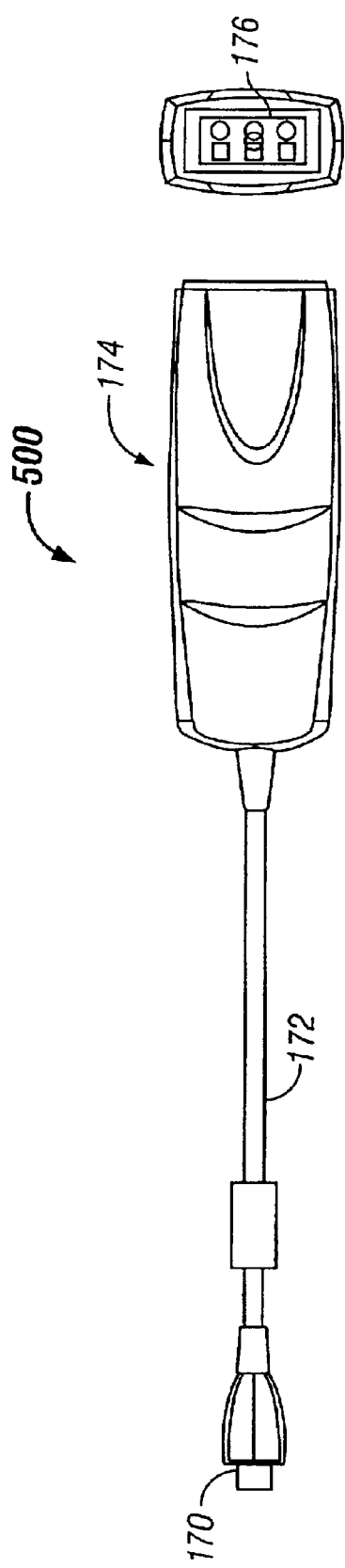
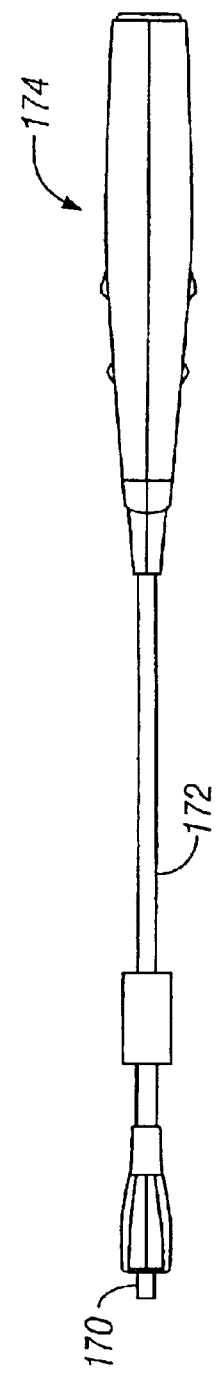
FIG. 1A
FIG. 1B
FIG. 1C

MEDICAL DIAGNOSTIC ULTRASOUND INSTRUMENT WITH ECG MODULE, AUTHORIZATION MECHANISM AND METHODS OF USE

CROSS-REFERENCES TO RELATED APPLICATIONS

This application is a continuation-in-part of U.S. application Ser. No. 09/840,002 filed Apr. 19, 2001, now U.S. Pat. No. 6,569,101, the full disclosure of which is incorporated herein by reference.

BACKGROUND OF THE INVENTION

1. Field of the Invention

This invention relates primarily to a handheld ultrasound instrument having various diagnostic modes and detachable modules. Also included is a means for manufacturer to strictly control the operational capabilities of the handheld ultrasound instrument after the instrument has entered the stream of commerce.

2. Description of the Prior Art

Modern ultrasound instruments generally fall into two classes of devices. Devices designed for diagnostic scans are utilized in hospitals and clinics and tend to be large, immobile devices. These devices require constant power such as from a 120 w or 220 w outlet. While some systems are arguably portable (being movable on a cart), they still rely on an external power source, and are limited by their ability to be transported easily. High end ultrasound systems are made with a large variety of operational features such as basic B mode and M modes scanning, as well as 2D and 3D Doppler imaging. Spectral analysis is a feature, usually implemented in software allowing more complete and accurate diagnostic examinations. Examples of spectral analysis techniques can be found in U.S. Pat. No. 5,647,366 (Weng) and 5,935,074 (Mo)—these methods require high processing power associated with real time spectral analysis.

Another aspect of high-end systems is they are afforded by their manufactures with an architecture capable of alteration. Either with the replacement of a system board, or the addition of specialized software, analysis, imaging, processing and data manipulation can be enhanced or improved during the life of the system.

A second class of ultrasound devices, relatively new in the field of medical ultrasound, are systems designed for handheld use. Systems on this type range in a wide variety of capabilities including those having single transducer pen elements that produce data in the form of sound waves or simple alphanumeric displays to devices using array transducers and having some what more complex displays in the form of an LCD device either in a specialized module (see U.S. Pat. No. 6,251,073 (Imran et al.) and U.S. Pat. No. 6,126,608 (Kemme et al.) or displays in laptop computers (U.S. Pat. No. 5,839,442 to Chiang et al.). For the most part, the miniaturization of ultrasound devices to create a handheld device has come at the cost of features found in high-end systems (such as combined 2D/3D Doppler with spectral analysis). Furthermore, handheld systems lack the upgrade path of larger systems during the life of the product, limiting a user to the purchase of new products in the handheld ultrasound market in order to obtain new capabilities.

Thus, it is an object of the present invention to provide a handheld ultrasound device with a wide array of ultrasound scan modes.

It is another object of the present invention to provide a handheld ultrasound device with a pulse wave (PW) scan mode.

It is another object of the present invention to provide a handheld ultrasound device with a continuous wave (CW) scan mode.

It is another object of the present invention to provide an ECG measurement tool for the augmentation of a Doppler ultrasound scan.

It is another object of the present invention to provide a handheld ultrasound device with the capability for performing spectral analysis on a Doppler image.

It is still another object of the present invention to provide a mechanism for the update of a handheld ultrasound device, such that accurate data can be maintained about the updates for the handheld ultrasound device.

SUMMARY OF THE INVENTION

In accordance with the objects of the present invention, a handheld ultrasound instrument is provided having a group of diagnostic modes not previously available in portable devices due to restrictions on both weight, and signal processing capabilities in small circuit devices. ECG capacity is also described using a separate module to preserve weight in the handheld instrument, as well as a secure control means for the upgrade and control of the diagnostic capabilities of ultrasound instruments while providing a means to maintain a detailed user database are disclosed.

The first embodiment of the present invention is a handheld ultrasound device weighing less than fifteen pounds, including a transducer, beamformer and image processor and a first digital signal processor capable of processing B mode and flow (2D Doppler) scans, having an second digital processor block comprising a digital Doppler QBP filter (FPGA) for filtering PW Doppler signals and a second digital signal processor core for PW Doppler signal processing.

The ultrasound instrument may also have the capacity for time-motion display, frequently referred to as M mode. M mode signal processing occurs on the first digital signal processor using a micro-code block, and the interpolation of M-mode signal for video display is done on the second digital signal processor.

The handheld ultrasound system may further comprise a CW Doppler circuit having a CW beamformer ASIC and a supplemental circuit for A/D filtering and performing analog to digital conversion on I and Q signal pairs, wherein the FPGA of the second digital processor block processes complex data at a constant sample rate prior to processing through the second digital signal processor core.

A method of performing spectral analysis on a Doppler image is also described.

In an embodiment of an ECG module, ECG functionality is added to a handheld diagnostic ultrasound instrument without significantly increasing the weight or cost of the instrument. More particularly, an ECG module is provided with a cable system connector for connecting the module to the handheld ultrasound instrument. The module includes leads for interfacing with a patient and the basic electronics for ECG signal processing including amplification and filtering of signals for use by the handheld unit. In a first embodiment the module includes electrical ground isolation for isolating the patient leads from the system signals and ground. The module houses the ECG electronics with a first stage amplifier and filter provided in the isolated portion of the module and all other ECG electronics provided in the handheld ultrasound instrument of the module.

Alternatively the first and second stage amplifiers and filters are in the ECG module, as well as a display signal processor, for formatting the signal into a displayable format. The display signal is then exported to the display of the handheld ultrasound instrument. The display export may be in analog format, or through an analog to digital converter, and exported as a digital signal. Amplified and filtered signals from the patient leads are optically coupled from the lead portion to the system portion of the ECG module. Necessary power for the lead portion is generated using either capacitive or inductive type power converters from the system power supply to the isolated portion of the ECG module. Thus the patient is not ground connected directly to the system ground reference.

More particularly, the power supply circuit includes a serial inductor for receiving a DC voltage and a shunt capacitor and a shunt switch connecting the serial inductor to a power ground. A first coupling capacitor capacitively couples the serial inductor to an isolated first power processing circuit, and a second coupling capacitor couples the power ground to the first power processing circuit. A rectifying circuit in the first power processing circuit includes a forward polarity diode connecting the first coupling capacitor to a first terminal of a positive voltage capacitor, and a reverse polarity diode connecting the first coupling capacitor to the first terminal of a negative voltage capacitor. An isolated reference terminal is connected to the second coupling capacitor and to a second set of terminals of the positive voltage capacitor and the negative capacitor whereby electric power is coupled through the coupling capacitors at the frequency of the shunt switch to the isolated signal processing circuitry.

A method of performing spectral Doppler is provided. The method of spectral analysis on a Doppler image comprised the steps of analyzing the display data to restructure the original power frequency spectrum, performing a temporal smoothing on the frequency spectrum, determining the absolute value deviation for each frequency spectrum, determining the mean power per frequency spectrum, applying one of several fixed smoothing filters to each frequency column, finding the maximum value before the mean of each frequency spectrum, establishing a frequency spectrum threshold, employing a peak finding algorithm, applying a fixed width filter for temporal smoothing and reversing the process of display data restructuring to return the image data to the size appropriate for the system display.

In accordance with the principles of yet another embodiment of the present invention, a diagnostic ultrasound instrument is provided with a software security mechanism that effectively restricts modification or replacement of software or data associated with the instrument. Updates to software or data for a particular type of instrument can be developed and easily distributed, but control over the actual update or modification of any specific instrument is retained.

In one embodiment, a "keycode" is generated via an algorithm that takes a unique system identifier and information regarding the modification or update to be performed as inputs. Software in the instrument to be updated prevents any update or modification of the instrument's software or data unless the correct keycode is provided by the person or agency performing the upgrade process. Requiring the person or agency performing the update to obtain the keycode from one or more authorized agencies allows the manufacturer to control such upgrade process to satisfy both regulatory and feature-control requirements. This mechanism does not require service personnel to perform the update process, nor is any movement of the instrument to an update facility required. Update software, data, and keycodes may be provided via a variety of mechanisms including portable memories, communication networks, facsimile, or voice and manual input via the instrument's user interface.

In a second embodiment, the ultrasound device has a software library located in a persistent memory. The software library is used for data and operational control. A security means is provided for enabling and disabling individual components of the software library.

In a third embodiment, a programmable ultrasound instrument is provided having a plurality of diagnostic modes. Access to the diagnostic modes is controlled through a gate flag registry. The gate flag registry can be modified through a verifying a keycode. The verification procedure utilizes a secure means for extracting hidden bits from the keycode. The keycode is based on one or more unique system identifiers.

The keycode is generated by a manufacturer or authorized agent utilizing a keycode generating program. The keycode encodes for the diagnostic modes to be enabled. Once the keycode is entered into the programmable diagnostic ultrasound instrument, the instrument executes the verification procedure on the keycode. The process allows the ultrasound instrument to decrypt the keycode and recover a large array of bits from the small keycode. These bits include the desired option bits (for enabling the desired diagnostic modes), error detection bits, and signature bits. The latter two used to verify the authenticity of the keycode.

Another embodiment of the present invention includes a programmable diagnostic ultrasound instrument having stored software and data for operational control. Part of the stored software is a software security mechanism that restricts modification of the software or data utilizing a 64-bit mixing algorithm and a bit-wise signature generator. The mixing algorithm and the signature generator each produce a bit string that is processed through a reversible logic operation. The resulted bit string is used to code for an alphanumeric keycode. The keycode can be "decrypted" by reducing the alphanumeric information into a bit string, then executing the reversible logic on the bit string to produce the two bit strings originally produced from the mixing algorithm and the signature generator. The two bit strings are verified against the originally produced bit strings via an encryption process inside the ultrasound instrument. If the bit strings are verified, then diagnostic modes are enabled (or disabled).

A system for tracking the diagnostic modes in programmable diagnostic ultrasound instruments is also disclosed. The system comprises a general purpose computer, ultrasound instruments and a data base. The computer has a program or logic board for generating a unique keycode for each programmable diagnostic ultrasound instrument. The keycode having encrypted error detection bits, signature bits and options bits for enabling diagnostic modes in a particular instrument. Each programmable diagnostic ultrasound instrument has a plurality of diagnostic modes that can be enabled or disabled upon successful verification of the keycode. The verification procedure utilizes a secure means for extracting hidden bits used to modify a gate flag registry from the keycode. Finally a data structure for centrally recording and tracking diagnostic modes of each diagnostic ultrasound instrument is used to keep track of every instrument, and their operational diagnostic modes. This system is useful in complying with government regulations covering medical devices, and ensuring a manufacture can maintain control over the operational features of the devices it makes or sells, as required by law.

In addition, a method of upgrading the functionality of a programmable ultrasound instrument is disclosed. The method comprises several steps. First entering instrument specific data and desired option data into a keycode generating algorithm. Second, generating a keycode using the keycode generation algorithm. Third, inputting the keycode obtained from the keycode generator into the programmable diagnostic ultrasound instrument, and fourth, verifying the keycode by running the keycode generation algorithm locally on the ultrasound instrument, but utilizing a "decryption" mode to compare and verify the signature bits, error detection bits and option bits.

These and other embodiment of the present invention will become readily apparent upon a detailed inspection of the detailed description of the invention, and a study of the appended claims.

BRIEF DESCRIPTION OF THE DRAWINGS

FIGS. 1A, 1B, and 1C illustrate an ECG module for use with a handheld ultrasound instrument.

DETAILED DESCRIPTION OF THE INVENTION

In reading the description of the present invention and its many embodiments, the following terms are used outside of their ordinary "dictionary" definition:

By "Keycode" we mean an alphanumeric or simply numeric character string used to represent an end user license for enabling a feature in the present invention. The "keycode" is the string of characters that a vendor or manufacturer of the present invention provides to a user for them to enter at a certain prompt of an ultrasound instrument. The keycode itself is an encoded character string, and when properly decrypted, yields large volume of instrument specific information for use specifically with an ultrasound instrument.

By "Ultrasound instrument" we mean any device specifically designed to use a transducer to produce and receive ultrasound waves for use as a diagnostic tool in evaluating a patient's medical condition or state. Ultrasound instrument refers in general to hand held portable ultrasound instruments weighing less than fifteen pounds. However one embodiment of the present invention applying to keycodes for use with ultrasound systems is specifically excluded from the under fifteen pound weight restriction and is meant for use with any ultrasound instrument.

An ultrasound instrument that is highly mobile is ideally suited for use with the present invention. The security and tracking system permits a mobile ultrasound unit to be tracked by its manufacturing serial number, and to have its full capabilities recorded in a central database regardless of where the instrument is located. Thus anyone who wishes to determine if an instrument has certain diagnostic features enabled on a particular mobile ultrasound instrument need only identify the unit by its serial number and call the manufacturer for the operational mode information. Mobile ultrasound instruments maybe more susceptible to tampering as they are may be taken to places outside of the proper control of a hospital or physician, and be tampered. Therefore it is helpful to illustrate a hand held portable ultrasound instrument in the context of the present invention.

Figure 1:
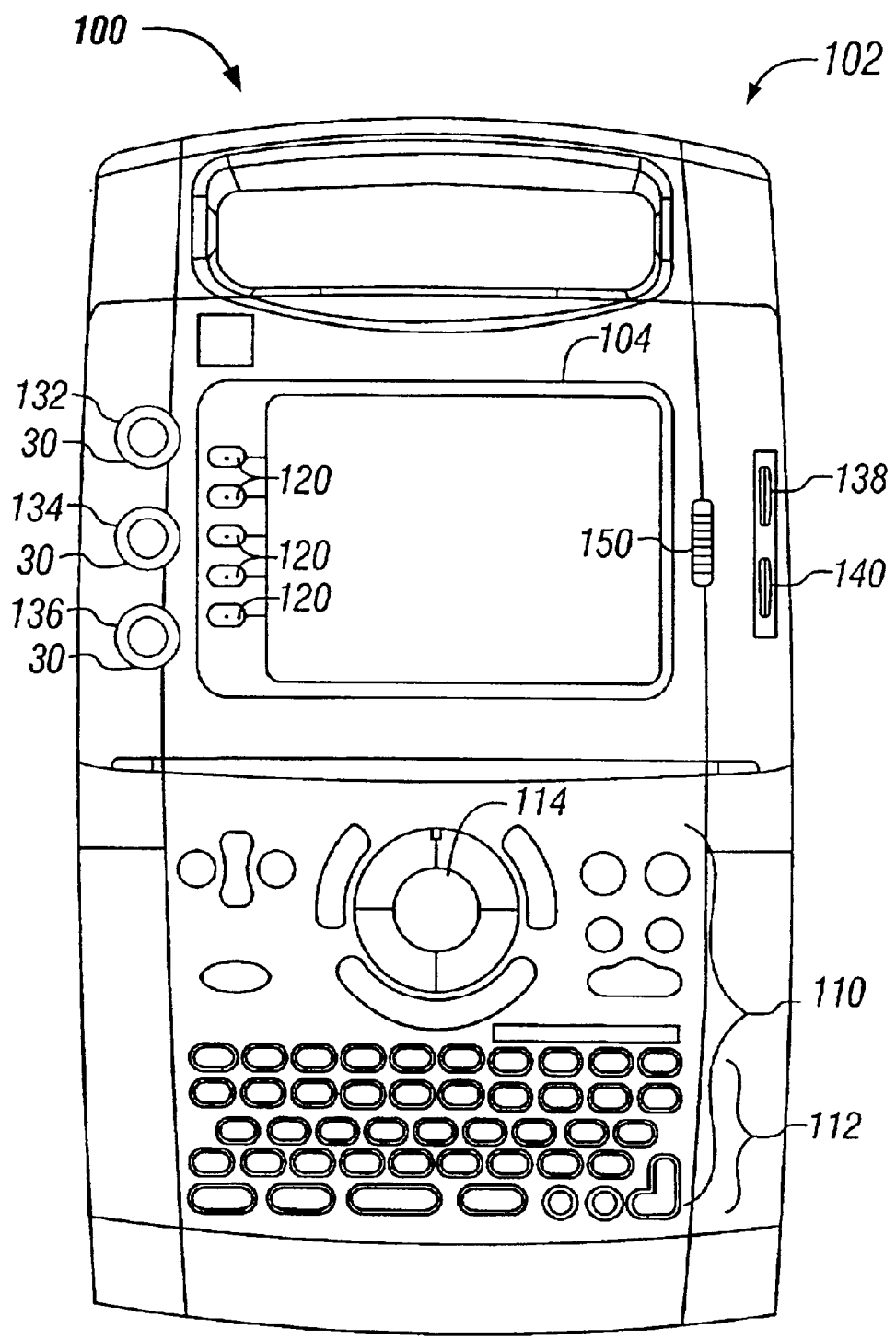
FIG. 1 is an exterior view of a hand held ultrasound instrument.

A highly mobile or portable ultrasound instrument having the security mechanism of the present invention incorporated into its architecture or software library is shown in FIG. 1. In general form, the ultrasound instrument 100 includes a handle 102 for easy carrying. The instrument has a separate transducer (not shown) for sending and receiving ultrasound waves. The received ultrasound waves are interpreted by the diagnostic programming executed on the hardware of the instrument 100. The resulting images are displayed on a display device 104. The display device may be any type compatible with the instrument, such as a LCD, or a passive/active TFT screen. Screens commonly use with laptop computers may be used for portable ultrasound instruments, while CRT screens, TV monitors or large high definition monitors maybe used with larger, non-portable systems. The ultrasound instrument usually has a control or user interface 110 with which a user can instruct the instrument 100 to perform a variety of diagnostic modes, or data analysis commands. The instrument has a QWERTY style keyboard 112 as well as a cursor controller 114 or "mouse" type feature. In a more specific design, an ultrasound instrument 100 incorporating the present invention also includes an array of visual controls 130 (such as near 132, far 134, gain 136, brightness 138 and contrast 140), and a group of menu keys 120 for allowing a user to make an easy selection of the more common programmed features of the instrument 100. A battery indicator 150 is included to permit a user to identify when the instrument 100 needs to be recharged, or when the battery should be replaced. An audible warning may also indicate when the battery is low. The instrument of the present invention has a speaker (not shown) built into the handle 102, and the handle acts as a sound chamber enhancing the sound quality. The display 104 is hinged so that it may be elevated from the main unit 100 during use for ease of viewing ultrasounds during operation.

FIG. 1B shows an external ECG module 500 such as one usable with the handheld ultrasound instrument 100. The ECG module 500 possesses an interface 170, cable 172, signal processing housing 174 and connector ports 176 for connecting ECG leads RA, LA and LL.

Numerous input/output ports are provided on the side of the instrument. An audio out, ECG receptacle that also provides serial data out (through a special adaptor), docking station data transfer, and video out. While the instrument of FIG. 1 illustrates an ultrasound device having the present invention integrated within, the present invention is not limited to the device as shown in FIG. 1.

Figure 2:
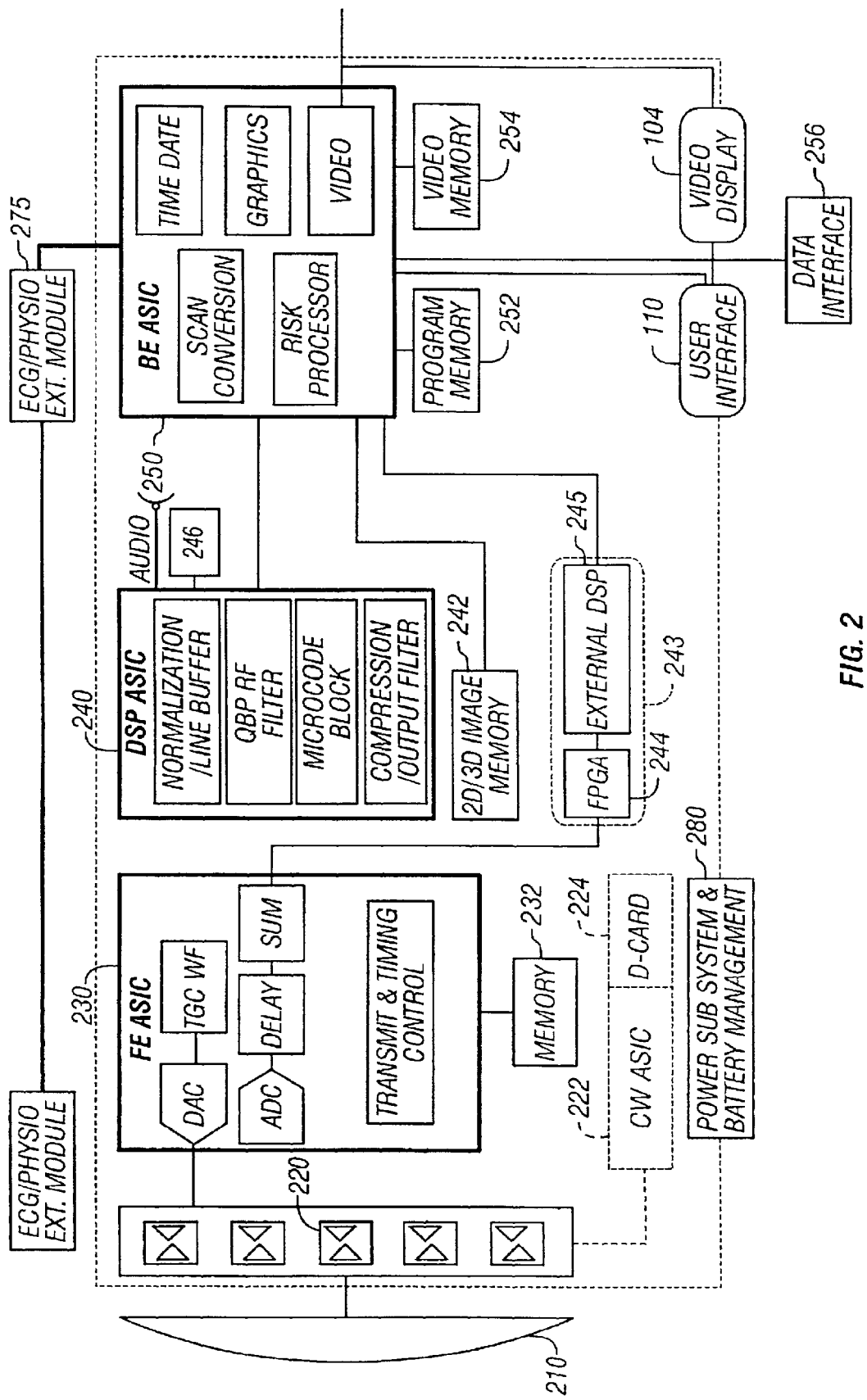
FIG. 2 illustrates a high level architecture block diagram of the present invention.

FIG. 2 illustrates the architecture of a hand-held ultrasound system of the present invention. A transducer array 210 is used for its solid state, electronic control capabilities, variable aperture, image performance and reliability. Either a flat or curved linear array, or a phased array may be used. The elements of the array are connected to a transmit/receive ASIC 220 which drives the transducer elements and receives echoes received by the elements. The transmit/receive ASIC 220 also controls the transmit and receive apertures of the array 210 as well as the overall signal gain and frequency response. The filter that sets the frequency response of the receive path may be a low pass filter to minimize alias artifacts due to the sampling of the data in the front end ASIC 230. Optionally, to support tissue harmonic imaging (THI mode), the filter may have a frequency amplitude response characteristic to equalize the energy of the harmonic and fundamental frequencies to facilitate additional signal processing in the blocks that follow. The filter in this case may have a topology similar to a high pass filter, band reject or band pass filter depending on the signal path characteristics desired. The transmit/receive ASIC is preferably located within inches of the transducer elements, preferably in the same enclosure and just behind the transducer. The transducer array 210 and T/R ASIC 220 may be located in a separate module, such as a detachable scanhead, or incorporated into the main body of the diagnostic ultrasound instrument. If the scanhead is detachable, it may be connected to the main body through a cable, or through a wireless connection means.

Echoes received by the transmit/receive ASIC 220 are provided to the adjacent front end (FE) ASIC 230, which beamforms the echoes from the individual transducer elements into scanline signals. The FE ASIC 230 also controls the transmit waveform, timing, aperture and focusing. In the illustrated embodiment the FE ASIC 230 provides timing signals for the other ASICs, time gain control, and monitors and controls the power applied to the transducer array, thereby controlling the acoustic energy which is applied to the patient and minimizing power consumption of the unit. A memory device 232 is connected to the FE ASIC 230, which stores data used by the beamformer.

Beamformed scanline signals are coupled from the FE ASIC 230 to the adjacent digital signal processing (DSP) ASIC 240. The DSP ASIC 240 filters the scanline signals and also provides several advanced features including synthetic aperture formation, frequency compounding, Doppler processing such as power Doppler (Doppler/color power angio) processing, and speckle reduction. The DSP ASIC provides signal normalization, QBP RF filtering, programmable micro-code block and a compression/output filter. An external memory unit is connected to the DSP ASIC 240 for use in temporarily storing processed data. A secondary DSP block 243 formed by an external field programmable gate array (FPGA) 244 and DSP core 245 also connect to the FE ASIC 230 to provide the ability to perform Pulsed Wave (PW) Doppler as well as support M-mode analysis. A separate memory 246 provides necessary memory storage for the DSP ASIC operations.

The information from the various diagnostic modes performed in either the DSP ASIC 240, secondary DSP block 243, or the optional ECG external module (see below), are then coupled to the adjacent back end (BE) ASIC 250 for scan conversion and video formatting and the production of video output signals. A memory device 242 is coupled to the BE ASIC 250 to provide storage used in 2D imaging and three-dimensional Doppler (3D CPA) imaging as well as intermediate backend information. The BE ASIC 250 also adds alphanumeric information to the display 104 such as time, date and patient identification. A graphics processor overlays the ultrasound image with information such as depth and focus markers and cursors. Frames of ultrasonic images are stored in a video memory 254 coupled to the BE ASIC 250, enabling them to be recalled and replayed in a live Cineloop™ real time sequence. Video information is available at a video output in several formats, including NTSC and PAL for television formats and RGB drive signals for an LCD display 104 or a video monitor.

The BE ASIC 250 also includes the central processor for the ultrasound instrument, a RISC (reduced instruction set controller) processor. The RISC processor is coupled to the FE ASIC 230, DSP ASIC 240 and secondary DSP block 243 to control and synchronize the processing and control functions throughout the hand-held unit. A program memory 252 is coupled to the BE ASIC 250 to store program data used by the RISC processor to operate and control the unit. The BE ASIC 250 is also coupled to a data port 256. The data port 256 may be a PCMCIA interface, a USB port or other information I/O line. The interface allows other modules and functions to be attached to the hand-held ultrasound unit. The interface 256 can connect to a modem or other communications link to transmit and receive ultrasound information from remote locations. The interface can accept other data storage devices to add new functionality to the unit, such as an ultrasound information analysis package.

The RISC processor is also coupled to the user controls 110 of the instrument to accept user inputs to direct and control the operations of the hand-held ultrasound instrument.

The power for the hand-held ultrasound instrument is provided by a rechargeable battery. Battery power is conserved and applied to the components of the instrument from a power subsystem 280. The power subsystem 280 includes a DC converter to convert the low battery voltage to a higher voltage that is applied to the transmit/receive ASIC 220 to drive the elements of the transducer array 210.

An alternative embodiment is the addition of a CW beamformer circuit 222, 224. The CW beamformer circuit comprises a combination analog and digital ASIC beamformer for CW processing and a daughter card for A/D conversion 224 (both shown with dotted lines). The CW ASIC 222 utilizes signal from the T/R ASIC 220, performs the CW beamformer operation and hands the signal to a daughter card 224. In operation the CW ASIC provides sixteen channels for the CW Doppler analog signal path. Each channel is connected with the FE analog ASIC 230 through the FE ASIC sum bus (not shown). The sixteen analog input channels are mixed down in quadrature to baseband using a Gilbert cell type mixer and a square wave local oscillator (LO) within each part. Each channel can be enabled independently and has independent delay control, but all LO channels have the same LO frequency and waveform. The waveform and frequency are globally programmable from 2–6 MHz. The outputs of the mixer are summed and wall/low pass filtered to provide a beamformed audio signal. The audio baseband output has additional processing through other parts of the invention.

The use of the CW ASIC allows a CW Beamformer to be incorporated on to a single chip providing advantages in the power consumption of the invention along with providing minimized space and weight used to handle the operation.

The CW ASIC handles significant digital and analog content in a single die, while isolating the digital and analog functions from cross over noise, allowing the use of very sensitive analog sections. The CW ASIC is low power with high sensitivity and a high dynamic range receive section.

Figure 3:
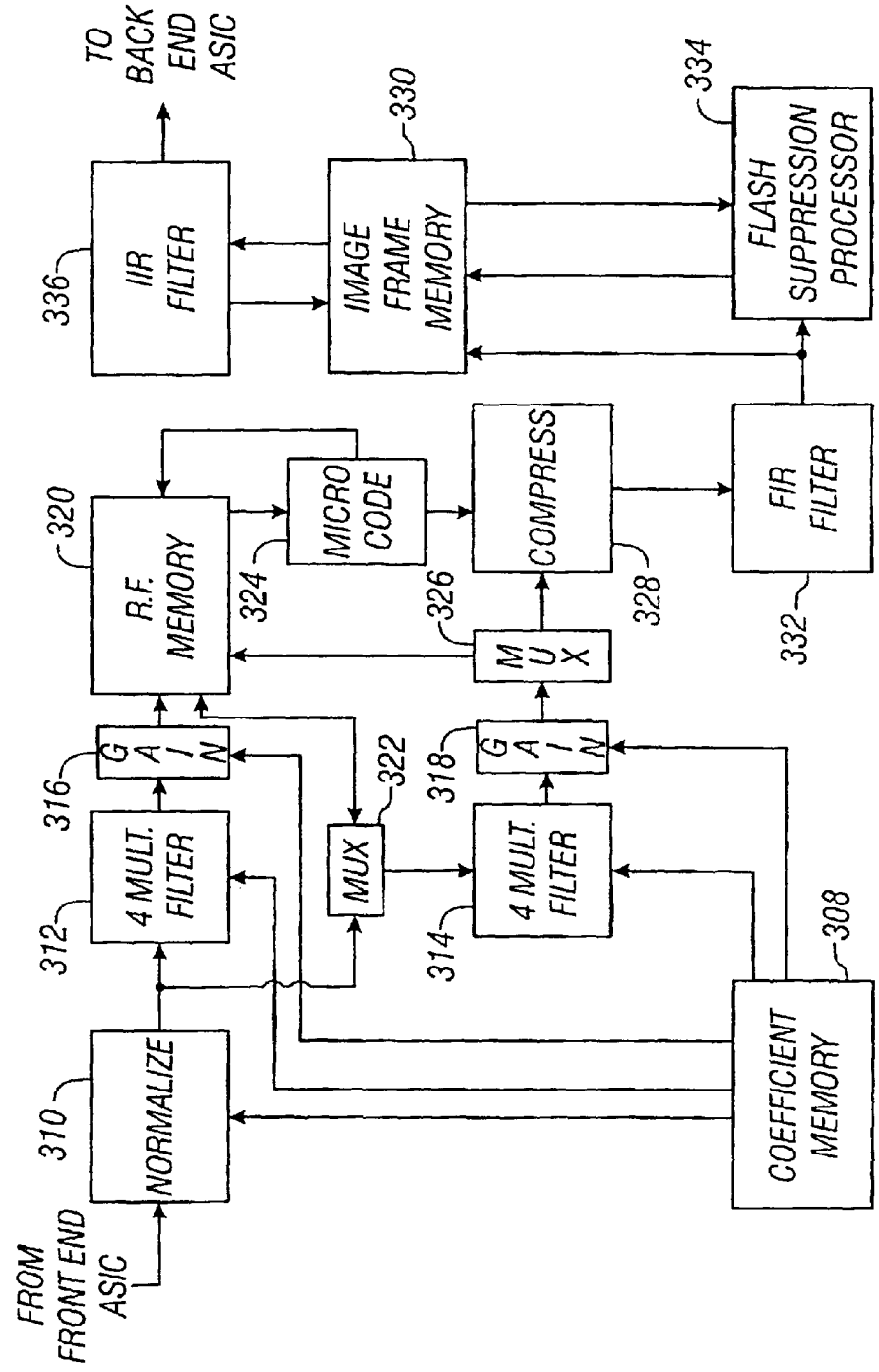
FIG. 3 is a block diagram of the primary DSP ASIC used.

Referring to FIG. 3, a block diagram of the DSP ASIC 240 is shown. Scanline signals from the FE ASIC 230 are received by a normalization circuit, where they are multiplied by a variable coefficient supplied by coefficient memory 308 to normalize the received signals for aperture variation. When the transducer is receiving signals along the scanline from shallow depths, a relatively small aperture, such as four or eight transducer elements, are used to receive echo signals. As the reception depth along the scanline increases, the aperture is incrementally increased so that the full 32 element is used at maximum depths. The normalization circuit will multiply the received scanline signals by appropriate coefficients over the range of aperture variation, such as factors of four or eight, to normalize the signals for this aperture variation effect.

Figure 5:
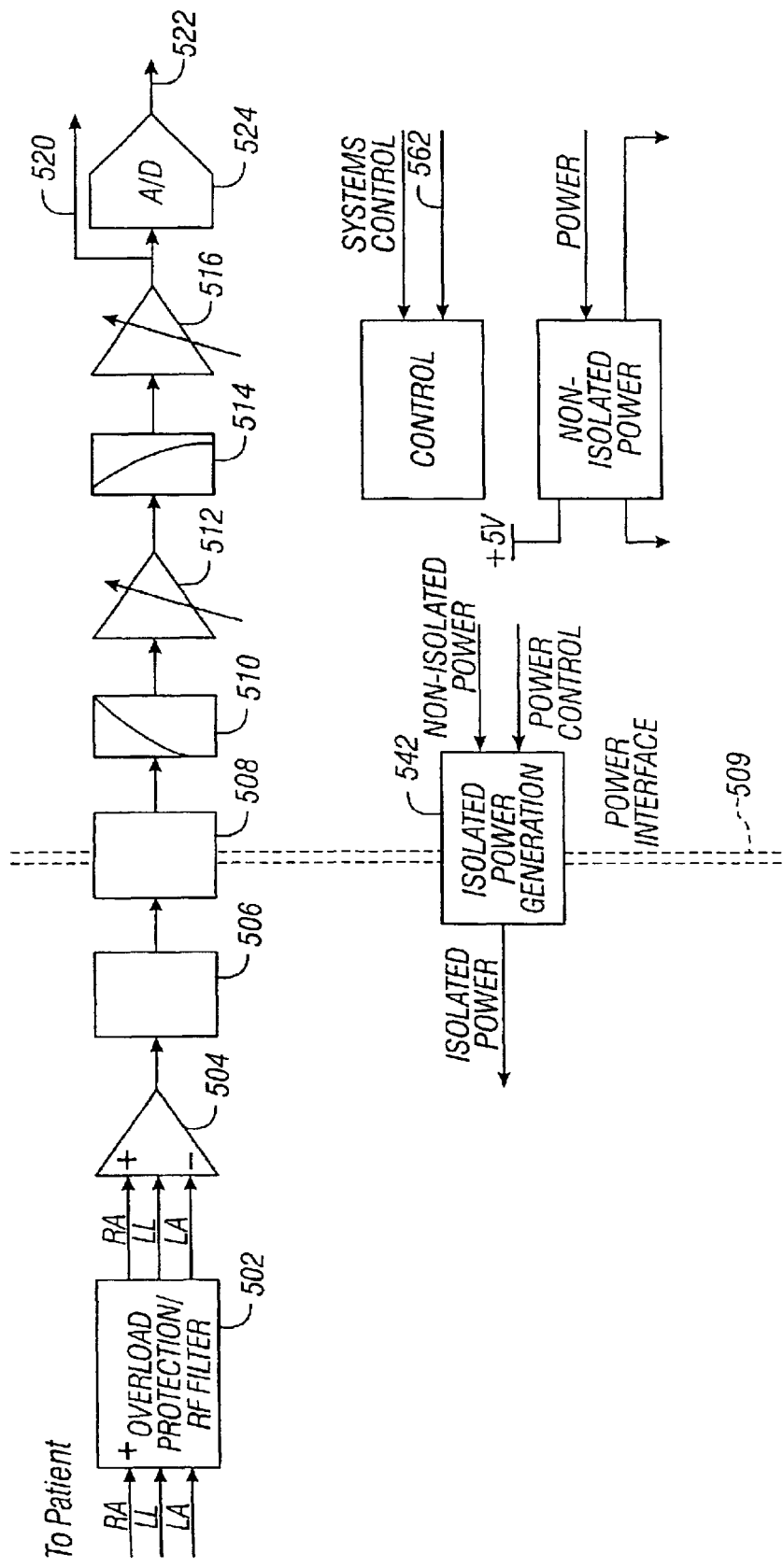
FIG. 5 illustrates a block diagram for an external ECG module.

When the ultrasound instrument is operating in the M mode to form a structural image of tissue and organs, the digital signal processor is operated as shown in the flow charts for M mode (FIG. 5). When the ultrasound instrument is operating in the 2D mode the normalized echo signals follow two paths, as in FIG. 2, one of which is coupled to a four multiplier filter 312 and the other of which is coupled by a multiplexer 322 to a second four multiplier filter 314. Each multiplier filter includes a multiplier and an accumulator which operate as an FIR (finite impulse response) filter. Scanline echo signals are shifted sequentially into a multiplier, multiplied by coefficients supplied by the coefficient memory 308, and the products are accumulated in the accumulator at the output of the multiplier. The coefficients for the filter 312 are chosen to multiply the echo signals by a cosine function and the coefficients for the filter 314 are chosen to multiply the echo signals by a sine function, to form a quadrature bandpass filter (QBP), preparatory for I and Q quadrature signal detection in the micro-code block 324 on the I/Q pair. The four multiplier filters produce accumulated signals at a rate which is less than the input rate to the multipliers, thereby performing decimation band pass filtering. When the signal bandwidth exceeds the display bandwidth of the display monitor. The image lines will flicker due to an aliasing condition. The decimation filtering is designed to reduce the signal bandwidth as well as the data rate to match the display bandwidth of the monitor. By applying a succession of input signals and coefficients to a multiplier and accumulating intermediate products, the effective length of the filter can be increased. For instance, input signals 1–8 can be sequentially weighted by the fourth multiplier and the products accumulated in the fourth accumulator; input signals 3–10 can be weighted by the third multiplier and the products accumulated in the third accumulator; input signals 5–12 can be weighted by the second multiplier and the products accumulated in the second accumulator; and input signals 7–14 can be weighted by the first multiplier and the products accumulated in the first accumulator. The data rate has thereby been decimated by two, and each multiplier and accumulator is effectively operated as an eight tap filter. This it is seen that the effective number of taps of the filter is a product of the number of multipliers (four in this example) and the decimation rate (two in this example).

Additionally, this filter reduces r.f. noise and quantization noise through its bandwidth limiting effects. I and Q echo signal samples are produced at the outputs of filters 312 and 314, amplified if desired by the multipliers of gain stages 316 and 318, then stored in the r.f. memory 320. The Q samples are coupled to the r.f. memory by a multiplexer 326.

When a synthetic aperture image is to be formed processing can be done in two manners, in the input RF domain after the normalizer block 310 or in the baseband domain after the QBP filter formed by 312 and 314. In the RF domain case the RF data points are stored from the first half aperture in r.f. memory 316 and added to the RF data points received from the second half aperture scanline. The resulting data is then filtered and processed in the normal manner as described above. In the Baseband case the I and Q samples after the QBP filter formed by 312 and 314 from the scanline of the first half of the aperture are stored in the r.f. memory 320 until the I and Q samples from the other half of the aperture are received. As the samples from the second half of the aperture are received, they are combined with their spatially corresponding counterparts by an adder (located in the micro-code 324). The size of this memory for the baseband case is kept to a minimum by storing the aperture signals after decimation filtering, which reduces the size of the memory required to store the scanline signal samples.

After the I and Q samples for the full aperture have been formed, the echo samples are analytically detected using the micro-code 324 and coupled to the compression circuit 328. The detected signal is compressed and scaled to map the detected signals to a desired range of display. Following detection and compression mapping, the signals are lowpass filtered in an FIR filter 332, then stored in an image frame memory 330. If the selected scanning mode (diagnostic mode) utilizes a single transmit focal point, the signals are transmitted back to the BE ASIC 250 for scan conversion. The signals can be frame averaged by an infinite impulse response (IR) filter 336 in the Backend Asic which utilizes image frame memory 330 as a frame buffer. If multiple focal zones are used, each received scanline segment is stored in the r.f. memory 320 until scanline segments from the entire display depth have been received. Preferably the scanline segments for one complete focal zone are acquired before transmitting and receiving segments from another focal zone. When all segments for a scanline have been acquired, each complete scanline is then read out of the memory and filtered by the FIR filter 332 which smoothes the boundaries between the segments for a more pleasing, artifact free image. A flash suppressor 334 is used to eliminate large frame-to-frame variations in the display signals.

Time-motion analysis, or M mode follows the same path as 2D data as described above until the micro-code block. In M-mode the micro-code block 324 performs a filter on a set, 4–16 lines, of QBP filtered lines and decimates the resulting output to the display scroll rate. The data is then compressed in block 328 before the data is handed off to the secondary DSP 244 which handles the display process and interpolation to the desired number of pixels for the display. Once the interpolation and display handling is complete, the signal moves on to the BE ASIC 250 for normal output.

Figure 4:
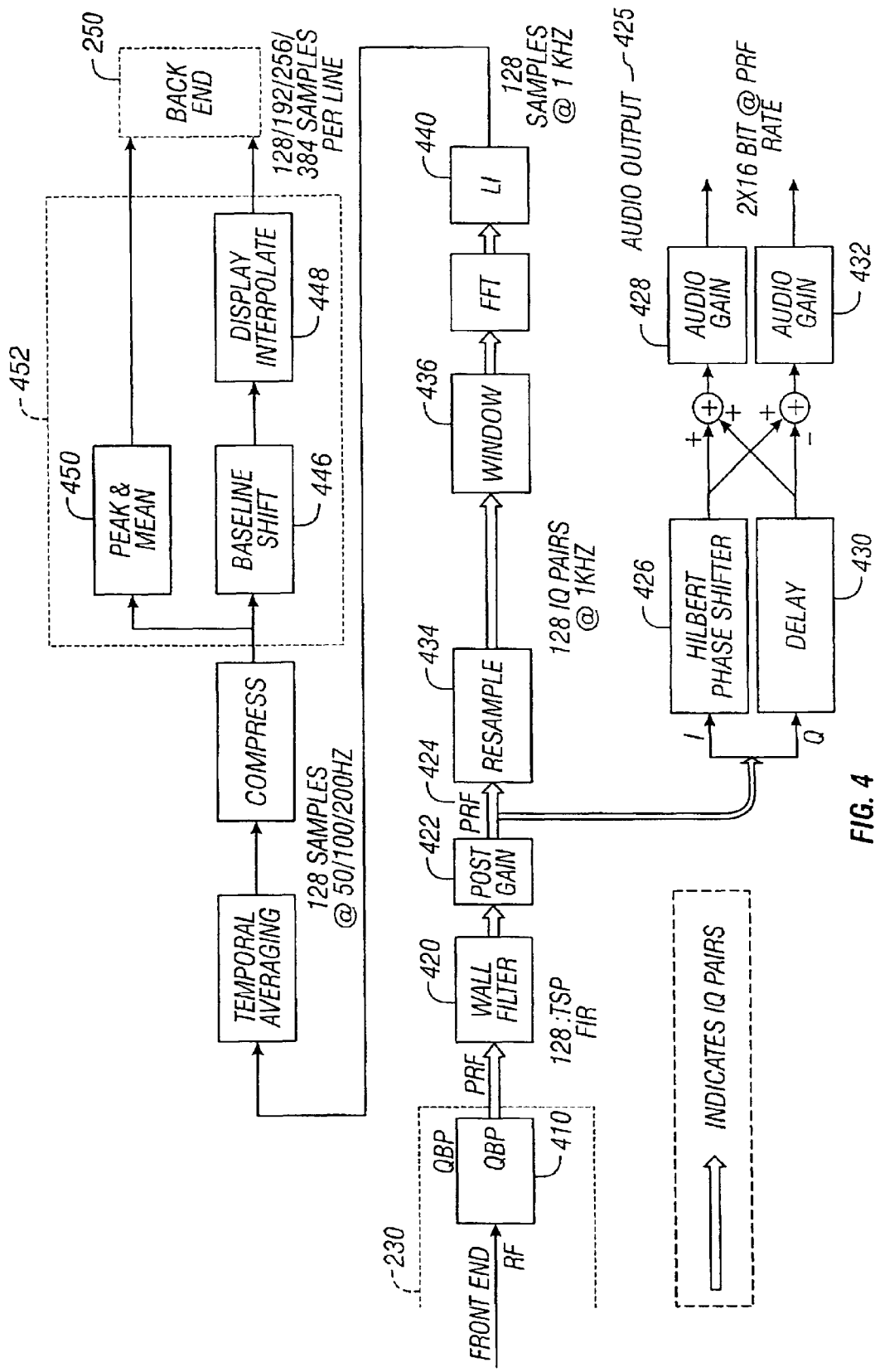
FIG. 4 is a block diagram of the secondary DSP used.

FIG. 4 illustrates a block diagram of the secondary DSP block 243 used for PWD mode. For PWD the QBP filter operations occur in a separate FPGA 244. In practice the operations of the external FPGA 244 and secondary DSP 245 can be combined in either a single ASIC , separate ASICs or a combination of ASICs and off the shelf components, such as DSP cores or FPGAs. For this discussion it is assumed a separate FPGA is used to interface to the FE ASIC and perform the QBP filter operation while the external DSP processor is used to perform the baseband processing after the QBP filter for PWD mode. As in 2D or M-mode the QBP filter 410 receives the r.f. signal from the FE ASIC and converts the signal into a baseband IQ pair. (note, when the CW ASIC is integrated into the system, the FPGA 244 receives complex signals at a continuous sample rate. If the PW Doppler mode is in use, the FPGA receives real signal at a discrete sample rate. Thus the FPGA 244 operates in one of two filter modes depending on the operation of the instrument.) The Baseband pair are sent to the DSP processor. The IQ pair are wall filtered by using two 128 tap FIR filters. The wall filter 420 is used to reduce static or slow moving clutter from the signal. The Output of the wall filter is coupled to the Post Gain block 422 to apply gain to scale the post wall filter data appropriately for the next processing steps. At 424 a duplicate IQ pair goes to both the spectral path resampler 434 and the audio output path represented by 426, 430, 428, 432.

In the audio output 425 the IQ pair is processed to create a left and right channels of sound. The I signal goes to a Hilbert Phase Shifter prior to proceeding to the sum/difference blocks. The Q signal goes through a delay 430 prior and the sum and difference signals are generated to produce the left and right outputs. Both Left and Right outputs are amplified by the same audio gains 428 and 438 to send to the audio amplifier to drive the speakers.

In the Spectral path the IQ signals from the wall filter are coupled to the Resample block 434 to generate IQ pairs at a 1 kHz rate. Every 1 ms N IQ pair enters the window block 436. N can vary depending on PRF rate and temporal resolution vs spectral resolution concerns. N typically will range between 64–256. The output of the window function is coupled to the complex fast fourier transform block FFT, which converts the signal from time domain to frequency domain. The frequency data is then coupled to the magnitude block 440 to generate the signed magnitude of the frequency output. The Frequency data is then averaged for smoothing effects and compressed in preparation for sending to the backend (ASIC) 250. The data next passes to the baseline shift block 446 to allow the display to be presented in a more effective manner for nonsymmetrical spectrums and finally the spectral data points are interpolated by 448 to the desired backend number of pixels for display. Additionally processing may also be done to generate the Peak and mean frequencies of the spectral data as shown in block 450. The additional information is also passed to the BE ASIC 250 for display on the scrolling display.

FIG. 5 illustrates an external ECG monitoring module that can be used with an ultrasound instrument of the present invention. The ECG module has three electrical leads for typical connection to a patient at the right arm, left arm and left leg (RA, LA and LL respectively). The connections to the right and left arms are used to measure the electrical potential across the chest during heart activity. The lead on the left leg is used as a reference as a signal. The electrical signals pass through the leads into the ECG module through an overload protection filter block 502. The block prevents any excessive potentials to damage the Differential Amplifier block 504 as well as filtering out of band energy to keep it from entering the circuit. The signals are then passed to the differential amplifier 504 for measurement of the electrical potential difference between the right arm and left arm lead using the left leg lead as a reference. The difference signal goes through a bandpass filter block 506 that eliminates signals outside the frequency range of interest and removes any DC offsets from the path up to that point. The signal is then coupled to the isolation block 508 which is necessary to protect the patient against risk of electrical shock hazard that might be present due to ground faults or other possible faults. The isolation block 508 may pass the signal across the isolation barrier 509 through an optical, magnetic or capacitive signal transmission means. The exact method of transferring data across the isolation barrier 509 is not particular to the present invention, as long as the method meets the ANSI/AAMI EC13 specification.

After passing through the isolation block 508, a highpass filter 510 eliminates resulting DC components or remaining low frequency energy and a first variable gain amplifier 512 can be used to boost the signal depending on the signal level. A lowpass/Notch filter 514 eliminates additional signal noise that may be present due to line frequency pickup (50/60 Hz and their harmonics) prior to moving to a second variable gain filter 516. The signal is then exported to the handheld ultrasound device 100 as either an analog signal 520, or a digital signal 522, after passing through an A/D converter 524. A user can control the gain of the signal from a gain control 136 in the handheld ultrasound device 100. The gain control 136 affects the signal both inside the hand held ultrasound device 100 in the image display unit 104, and at the two variable gain amplifiers 512, 516.

High pass filter 510 on the system side of the isolation block 508 removes the lower frequency component and biases from the signal isolation block output for the received ECG signal. It is a first order high pass filter 510 with a frequency cutoff set at 0.07 Hz. The signal from high pass filter 510 is then passed to a variable gain amplifier 512 that has a gain of from 1 to 8 with a center frequency at 100 Hz. The amplified signal from the variable gain amplifier 512 is then passed through a low pass/notch filter 514, having a center frequency of 30 Hz, and then to a second variable gain amplifier 516 with a gain of 1 to 8 and a center frequency at 50 Hz. The amplified signals are then exported to the handheld unit 100 as either an analog signal 520, or digital signal 522 through an A/D converter 524 within the system in unit 100 for application to and use by, the system processor.

In accordance with the present invention, power to the ECG electronics is applied through a power interface 542, which capacitively couples modulated power signals to amplifier 504. In specific embodiments, the DC power from the system can be either +16 volts or +9 volts. The power clock to interface 562 is received from the system in handheld unit 100.

The ECG module is either self powered using an isolated power supply, or powered from the main unit using a power subsystem and a isolated power generator so that only isolated power is fed to the elements on the patient side of the electrical isolation barrier.

Figure 6:
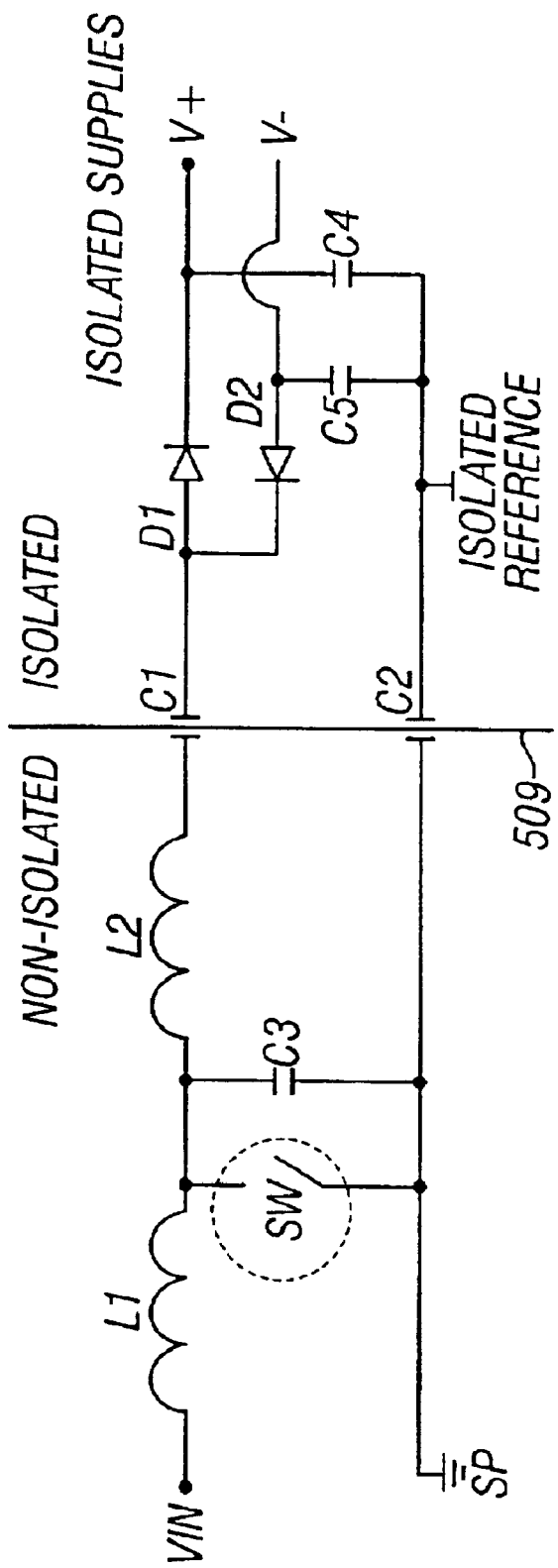
FIG. 6 illustrates a power scheme for an external ECG module.

FIG. 6 illustrates and example of a possible power scheme for an external ECG unit. The system power from the handheld unit is connected through serial connector inductors L1 and L2 to a first isolation capacitor C1. The common terminal of inductors L1 and L2 is connected via optional capacitor C3 and a transistor switch SW to the ground terminal of the system power. Switch SW is controlled in response to the power clock in chopping the system power at a frequency suitable for coupling through isolation capacitors C1 and C2 to the isolated electric circuit in module 500. The first coupling capacitor C1 is connected through a forward biased diode D1 to a positive charge storage capacitor C4, and isolation capacitor C1 is connected through a reverse bias diode D2 to a negative charge storage capacitor C5. Isolation capacitor C2 couples the system power ground to an isolated reference terminal.

The coupling capacitors allow for a very high frequency operation of the power interface. High frequency operation also allows the use of small capacitors and inductors on both sides of the isolation boundary, thus further reducing the size and weight of the ECG module. A resonant topology as shown also reduces EMI considerations since some switching voltage will be present on the isolated reference due to the capacitive coupling impedance of the ground planes and the switching currents circulating across the isolation boundary 509.

A high frequency operation is also required to allow the isolation capacitors to be small in value and guarantee the isolation impedance is sufficiently high to pass the energy required for the isolated power supplies without having the voltage present at the switching frequency on the isolated reference to fail the leakage current at that frequency. The allowed leakage currents increase with frequency.

The capacitors must be rated at a voltage which is large enough to pass the various safety tests, and rated at 5 kv or greater if defibrillation protection is desired. Surface mount capacitors are commercially available which must meet these requirements in a cost effective small and lightweight package. The use of capacitive coupling permits isolation of the power supply from the diagnostic system in accordance with medical safety applications.

Tissue harmonic imaging (THI) allows the reduction of signal clutter and near field effects. The normal 2D path components as described above are used for THI, but the blocks are programmed in a different manner. In THI the receive path QBP filter in block 312 and 314 will be programmed to receive energy at the second harmonic of the transmit spectrum. The Front End transmitters will be driven at a frequency near the low band edge of the transducer to allow the second harmonic energy to fall within the upper edge of the transducer frequency response. Some fundamental energy may also be utilized by shaping the QBP filter to fill out the image across the entire display depth due to the higher attenuation of the second harmonic energy with depth.

Figure 7:
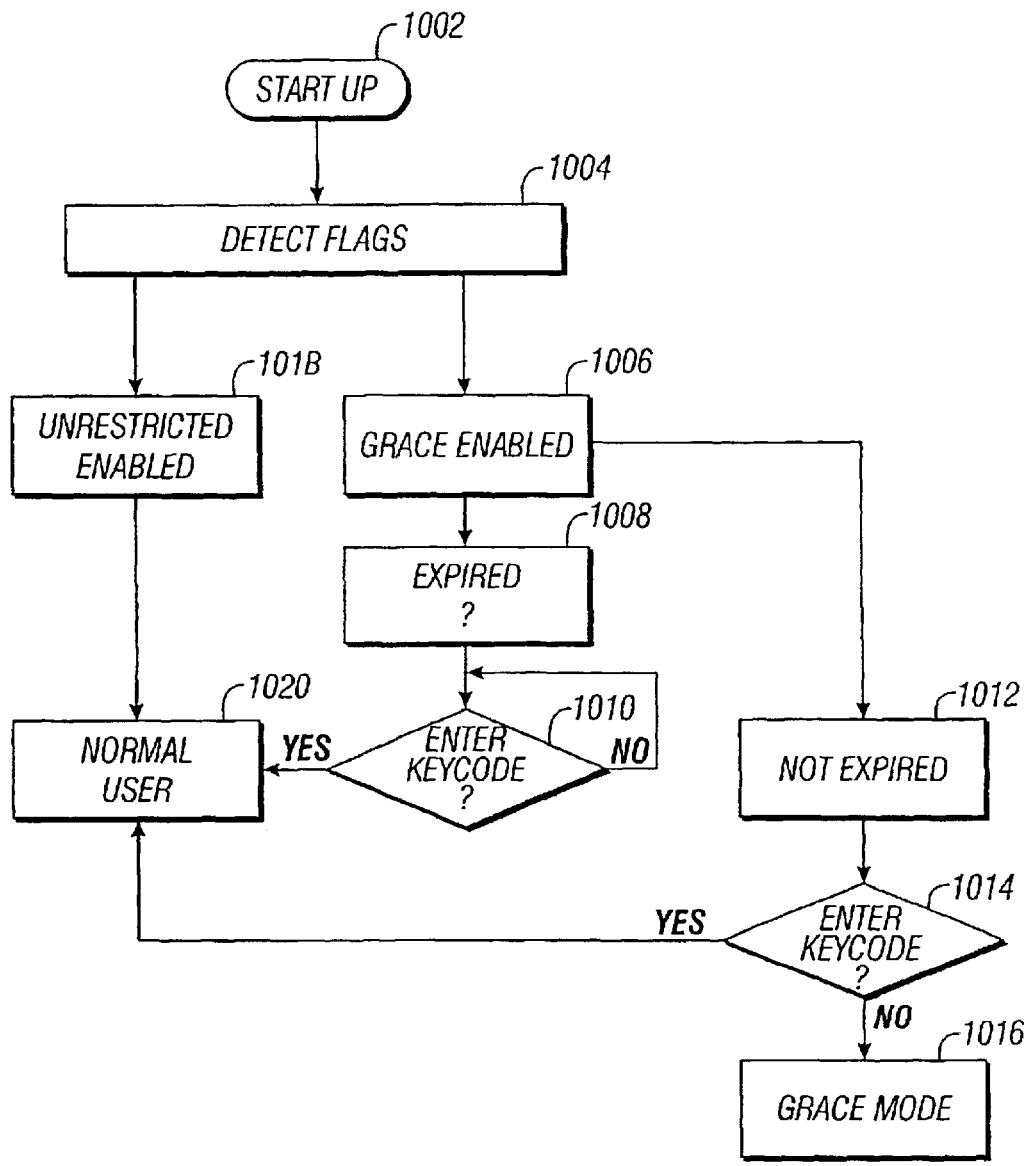
FIG. 7 shows a flow chart overview of the license manager.

FIG. 7 illustrates an overview flow diagram of the license manager 1000 used in the present invention. Once the ultrasound instrument of the present invention is turned on, the system goes through its normal startup routine. During this procedure, the system checks for the operational mode of the device, established by a registry of gate flags. The gate flags identify to the system whether the unit is operating in unrestricted mode (normal mode) or a grade period mode (grace mode) as well as detecting the gate flags for the software that is enabled within the instrument. The principle gate flag is to determine if the operational mode is enabled as open (gate encoded as 1) or if the operational mode is encoded as "grace" (gate encoded as 0). If the operational mode is encoded as open, then the device operates in normal mode with the gate flag registry scanned so that all other diagnostic modes are scanned for a determination of whether the mode is enabled (gate flag set to 1) or disabled (gate flag set to 0). If the operational mode is set as "grace", the instrument will still run through a scan of the gate flag registry. Any enabled modes detected will now run in grace mode—they are available for use for a limited time as determined by the grace period. Once the grace period expires, those modes are disabled.

Figure 10:
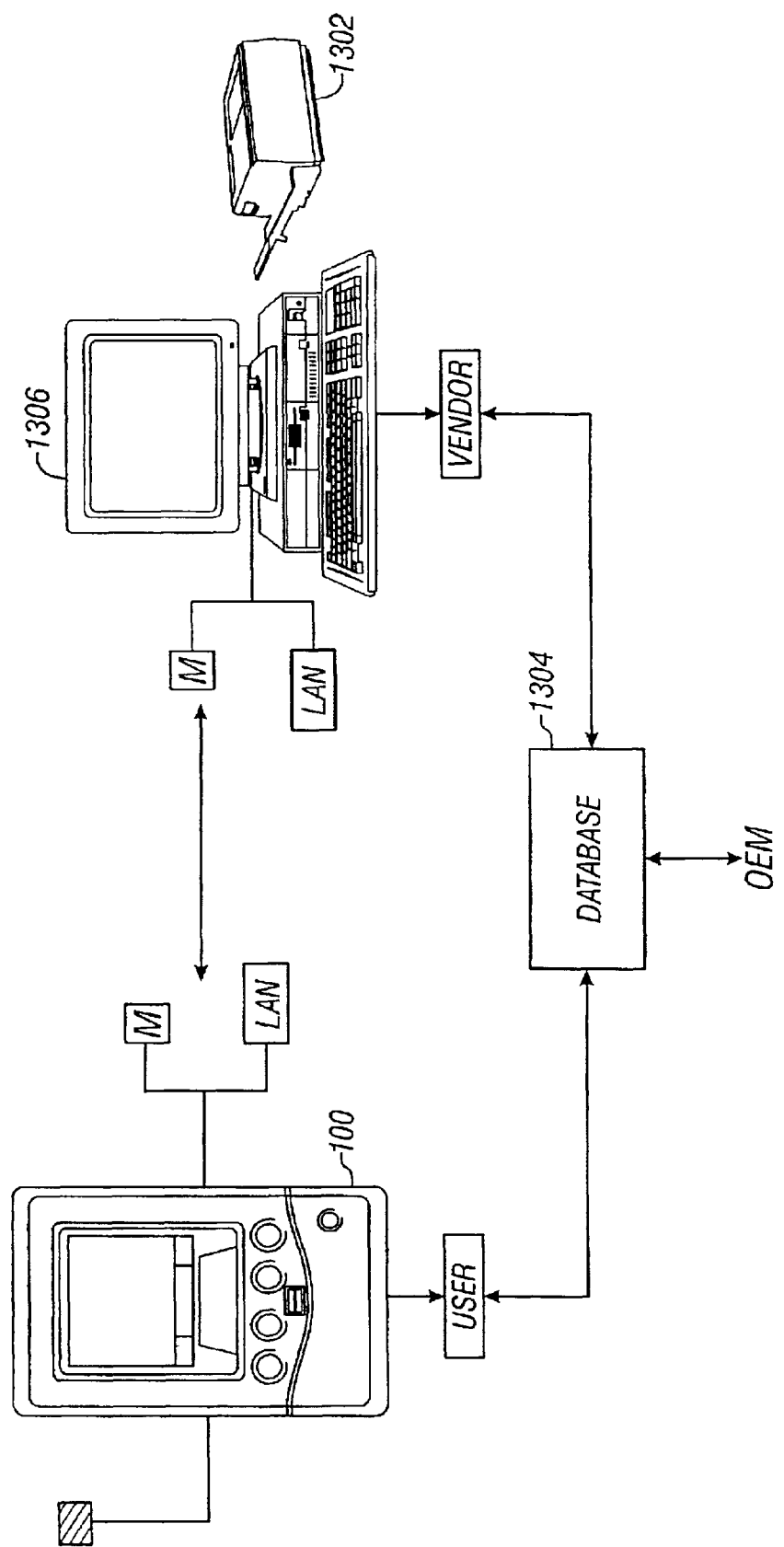
FIG. 10 shows a system incorporating the elements of the present invention for tracking individual unit capabilities.

As shown in FIG. 10, the system goes through a startup routine 1002 when it is turned on. The system checks for the operational mode 1004, a gate flag set to either 1 or 0. If the operational mode 1004 gate flag is set to 1 (it is enabled), then the system enters unrestricted mode 1006. The system then proceeds to check for enabled application software or diagnostic modes 1008. Each diagnostic mode has a corresponding gate flag that is either set for 1 (enabled) or 0 (disabled). All the applications that are flagged as enabled are available to the user for normal use 1012.

If the unit detects the system is operating in grace mode 1020, the system checks the system clock against the preprogrammed grace period 1022. The grace period may be established in number of hours of run time for the system, number of hours of run time for a particular option, or number of hours since the grace period started (which would include time the system was turned off). Once the system has checked the grace period against the system clock, it will prompt the user 1026 to enter a keycode 1150 that will permit the unit to operate in normal mode 1012 without any additional prompts for a keycode. If the user enters a valid keycode 1150 and enables the unit for normal use 1012, the system will switch over from grace mode 1020 to normal mode 1012. If the user fails to enter a valid keycode, the system will either operate normally as long as the grace mode has not expired, or if the grace mode has expired, it will prompt the user to enter a valid keycode. If the user attempts to bypass the keycode entry screen, the unit will either shut down completely, or operate in a restricted normal mode where previously enabled applications are available to the user, however any "trial period" applications will not operate. A description of how the unit is enabled through the keycode licensing system follows.

Figure 8:
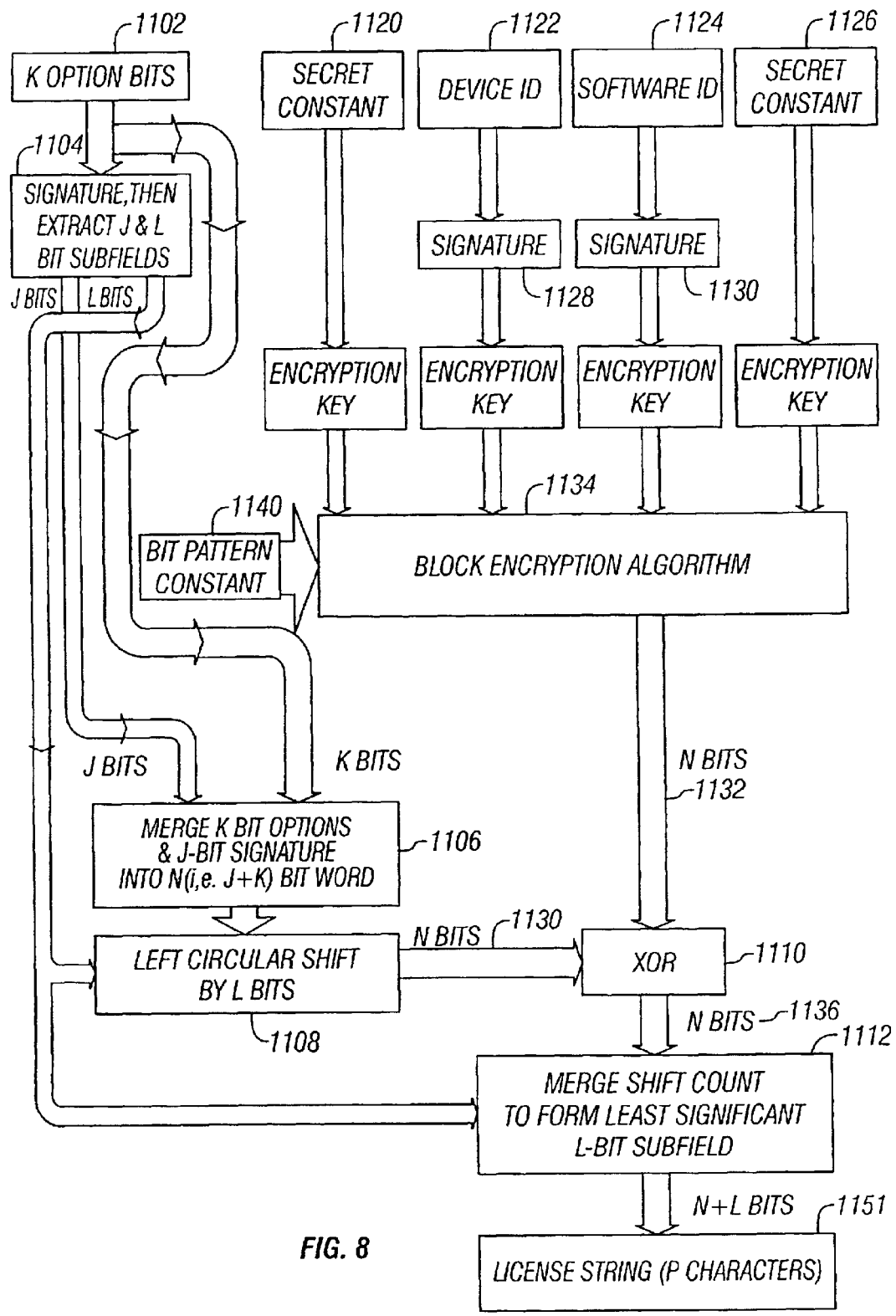
FIG. 8 shows a detailed flow chart of the license generator.

FIG. 8 illustrates the keycode encryption algorithm utilized by the system in GOM. The algorithm shown is a combination of a signature generator 1104 and an encryption algorithm 1134 combined with a reversible logic operation 1110. In this process, a user selects one or more software features the user would like to enable in a programmable diagnostic ultrasound instrument. That information is provided to the manufacturer of the instrument, or their authorized agent. The software enabling request is converted into a code for entering into the keycode encryption algorithm. The code carrying the software enabling information becomes the options bits 1102 (containing some variable of K bits). Following the logic of the algorithm, the option bits 1102 are sent to a signature generator 1104 where the bit string is separated into a pair of sub-field bit strings, labeled J and L. An intact K option bit string is sent to a merge operation 1106 that merges the K bit string with the J bit string into an N bit word. The N bit word is then sent to a circular shift 1108 (which may be any bit shift process, but here is labeled a left shift) wherein the shift is equal to L bits. The circular shifted N bit word becomes a first N bit string 1130 and is passed on to the reversible logic process 1110 (X-or operation shown here).

A second N bit string 1132 is generated using information specific to the instrument to be upgraded. This information involves parameters unique to the particular device, such as a device ID 1122 (serial number or other identifier), software build ID 1124, or other identifier assigned to the instrument during the manufacturing of the device. The unique device identifiers are combined with one or more secret constants 1120, 1126 (two in the example shown) and the unique identifiers and secret constants are used as the encryption keys for a block encryption algorithm 1134 (TEA, or others). To generate the necessary output bits for the reversible logic operation 1110, a bit pattern constant may be utilized in the block encryption algorithm. The encryption algorithm 1134 executes its logic on the input of the various encryption keys and optional bit pattern constant 1140 to produce a second N bit string 1132. The second N bit string 1132 is sent to the reversible logic process 1110 for a creation of a third N bit string 1136. The third N bit string 1136 is processed through a merge shift count 1112 using the L bit sub-field produced in the signature generator 1104. The result is a N+L bit string that is converted into a keycode 1150 of alphanumeric (or simply numeric) characters. Since the characters coded for in the keycode 1150 may use a large number of bits, the keycode 1150 can be relatively short while the N+L bit string is very long.

While either alphanumeric or simple numeric keycodes can be generated, there are practical limitations to an alphanumeric keycode. An alphanumeric keycode (keycode) cannot be easily distributed to foreign countries where the language base does not support the same alphabet as the manufacturer or authorized agent of the ultrasound instrument. For the manufacturer, an alphanumeric scheme may be used domestically, or in countries with a common alphabet. However for location where the product is used where the alphabet is not the same, a simple numeric keycode must be used. In either case the length of the license will still provide the use of the fall length of the N+L bit string.

The logic shown utilizes a single signature generator 1104 and a single block encryption algorithm 1134. However the effectiveness of this type of keycode generation system is by no means limited to using only one of each type of algorithm. Computationally a processor can as easily handle a keycode generation system that involves a plurality of signature generators and encryption algorithms. The base component that is required regardless of the combination of algorithms used is to provide for the reversible logic operation to mix the bits of the various bit strings that are produced so that it is essentially impossible for an unauthorized person (e.g. some one trying to hack the ultrasound software) from enabling features in the instrument which have not been paid for, and cannot be tracked as required by government regulations. Thus the use of the encryption algorithm as a pseudo-random number generator, combined with a signature generator to produce an option string with a series of non-option encoding bits, combined with the reversible logic (X-OR) process, permits the generation of a strong, safe way to transmit a license code through any channel which cannot be decrypted by an unauthorized user. The use of this process allows the device to recover all the necessary option bits upon reversing the procedure.

Figure 9:
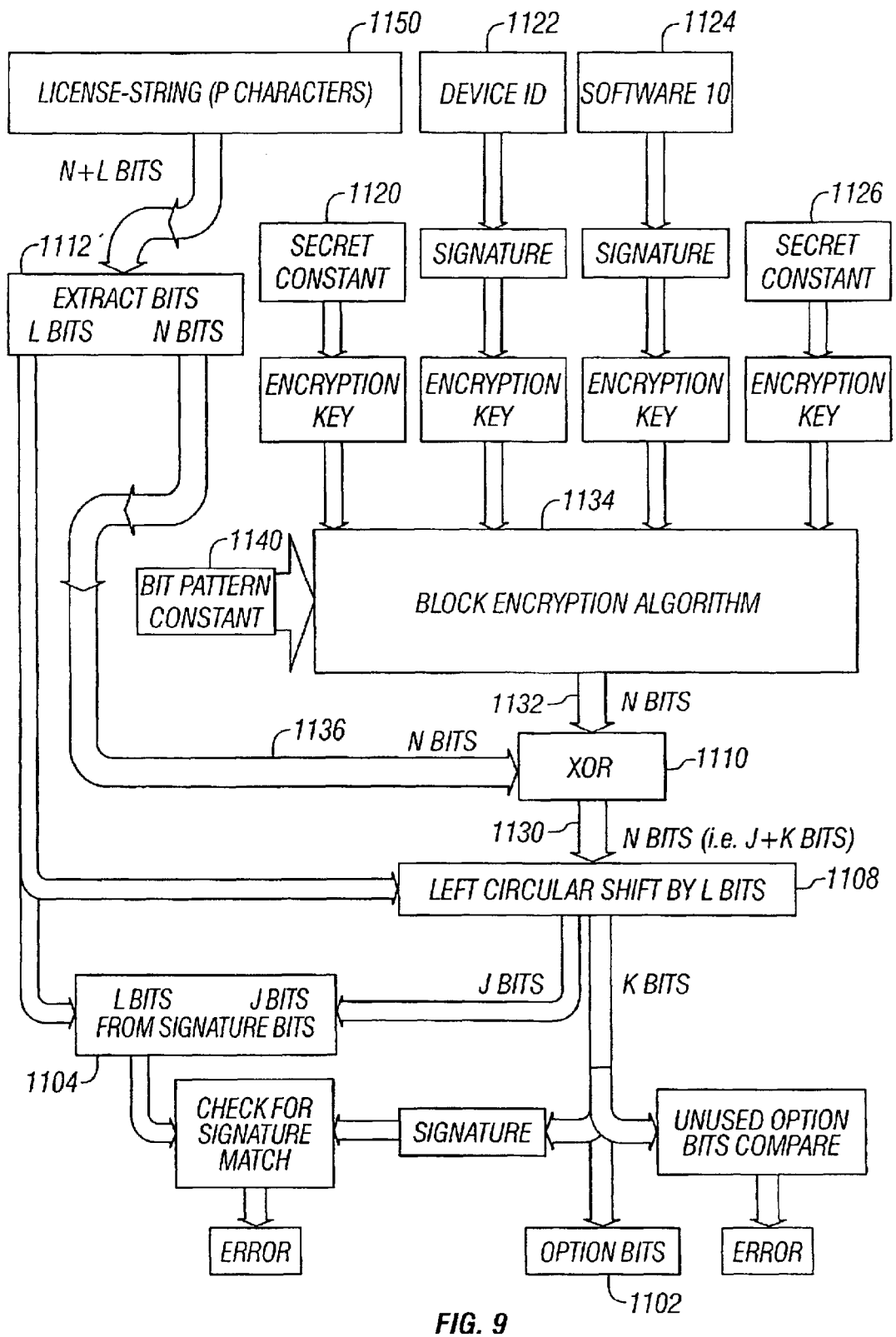
FIG. 9 shows a detailed flow chart of the license decryption algorithm.

FIG. 9 illustrates the process through which the keycode is verified by the ultrasound instrument implementing security mechanism of the present invention. The keycode 1150 generated (FIG. 11) in the license generator 1100 is entered into the instrument by a user at the new license entry prompt 1018. The keycode of P characters 1150 encodes the N bit word and the L bit string from the license generator. The instrument has the same logic operations programmed into it as are used in the license generator (FIG. 11) and is able to extract L bit string and the N bit word from the P character keycode 1150. The N bit word 1136 is used by a reversible logic process 1110 (X-or) to reverse the logic process of the license generator. The second N bit string 1132 that was originally produced by the block encryption algorithm 1134 is produced by an identical operation within the ultrasound instrument. The second N bit string 1132 is used with the N bit word 1136 in the reversible logic operation to reproduce the first N bit string 1130.

From this point the L bit string extracted from the keycode 1150 of P characters is used to extract the relevant signature bits, error detection bits and option bits. By using the reversible logic process 110 and the combination of a signature generator 1104 and block encryption algorithm 1134, it is possible to extract a large number of bits from a small number of characters in the keycode. The various bit patterns must match up precisely to produce the signature, error detection bits and option bits 1102. The option bits 1102 are then used to identify which gate flags of the system registry are to be marked "open" or "closed" thus enabling previously dormant software resident in the ultrasound instrument.

In conjunction with the keycode system of the present invention, the ultrasound device may have a software application made available to a user through uploading through an external hardware element, such as a detachable scanhead. This is particularly useful when a new feature requires a new hardware element such as a specialized scanhead (e.g. for neonatal examinations) or a specialized diagnostic module (such as an ECG attachment). In this instance the software application is automatically loaded from the scanhead (or attachment) to the main ultrasound unit 100. The unit detects the new scan head either at startup, or during a peripheral device check routine. When the new scanhead is detected, the system automatically detects software that is not already part of the software library. The new software is download from the scanhead into the main software library and enabled for use during a fixed grace period. The customer is permitted to try the software during the grace period and enter a keycode specific to the software downloaded from the scanhead. In the event a valid key is entered into the ultrasound instrument the grace period switches over to unrestricted use, and the user is able to use all functions that have been paid for without any concern for running out of the trial period. However if the proper keycode is not entered into the ultrasound instrument, the ultrasound instrument will not startup as normal during the start up procedure (at the expiration of the grace period). Instead the ultrasound instrument will automatically prompt the user for the proper, unit specific keycode that will allow the unit to be used in unrestricted format. If the user fails to enter the proper code, the ultrasound instrument will automatically go re-prompt the user for a keycode. Alternatively the unit might be programmed to shut down, or enter a "sleep" mode. Use of information specific data to a particular unit permits the proper unit to be enabled with the desired features. Use of the same keycode on another unit will not generate an authentication bit string. This insures that each keycode issued by the manufacturer prevents the enablement of features on a different unit. It also permits the manufacturer to maintain a precise database of the capabilities of each instrument since each instrument may only be upgraded through a keycode made available from the manufacturer. Although the instrument itself has the ability to verify a keycode, it does not have the ability to generate keycodes on its own, and the unique elements to each instrument would not permit some one to "hack" one instrument to yield a security scheme to enable other instruments of the same type. It is also possible for the user to contact the vendor for a license code that will disable the application that has placed the instrument into the GOM and return to unrestricted use of the previously purchased applications without enabling any new features.

While the processes described above are principally executed through software, an alternative embodiment of the present invention utilizes the same operations within the program of an application specific integrated circuit (ASIC) wherein the ASIC chip retrieves the necessary input values to perform the logic of producing and verifying a keycode or keycode from one or more registers containing the necessary information. In this manner the ASIC mimics the same logic as the software previously described to achieve the same result. The ASIC may be programmed with additional features such as a feature verifying download to a keycode database in order to enable or disable any applications within the software library.

FIG. 10 illustrates a system incorporating the license generator and an ultrasound instrument of the present invention. The system incorporates a general purpose computer 1306 having a license generator 1100 for receiving the required information from a user necessary to create a keycode 1150. Once an operator has entered the necessary instrument specific information provided by a client, a keycode 1150 is produced that is provided to the client. The transmission means of the keycode to the client can be in any format, including a public distribution since the keycode has no value to anyone except the client. The vendor may receive the request through a dial-up connection using a modem M or through an internet connection LAN, or the user may call the vendor by phone 1302 and the vendor can manually input the information into the keycode generator. The client then enters the keycode into the unit for which the upgrade is desired. The instrument runs through the decryption process to produce the first N bit string and validates the keycode. Once the keycode has been validated, the instrument 100 now operates with the desired features. The vendor or manufacturer can update his records in his central database 1304 with the newly enabled features of the ultrasound instrument 100 allowing the manufacturer to maintain a complete and accurate log of all the instruments sold and their operational capabilities. Using this system the manufacturer is able to keep accurate records of the capabilities of all the instruments sold. The manufacturer may be the same entity as the vendor, or the vendor may perform the keycode generation and report the information back to the manufacturer.

Figure 11:
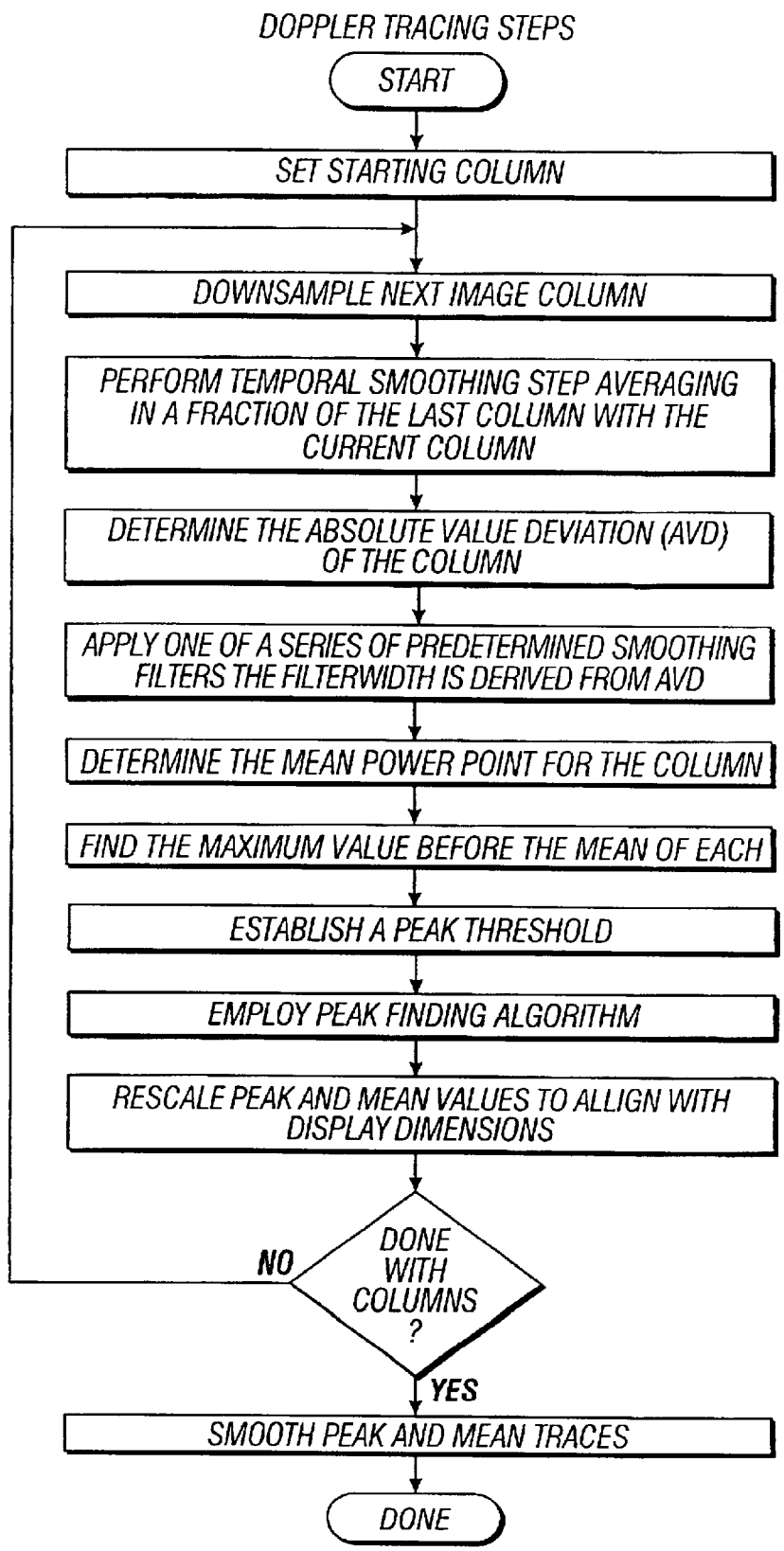
FIG. 11 illustrates a flow chart of the method of providing spectral analysis on a Doppler image.

FIG. 11 illustrates a flow chart corresponding to a method of performing a spectral analysis on the Doppler image created by the present invention. The method of performing a spectral analysis comprising the following steps:

(a) Analyze the display data to restructure the original power frequency spectrum.

Limitations in power available and real estate of a processor in a small, hand held system naturally require a different approach to spectral analysis than on large, fixed devices without the same constraints. In the present invention, the image data derived from the 2D/3d Image memory 242 is fed into the RISC processor of the BE ASIC 280. Within the RISC processor, the Doppler spectral data is compressed to reduce the number of frequency spectrums that must be analyzed. The compression can be severe, in that the total Doppler spectrum may be reduced by an order of magnitude or more, however the less compression that is utilized, the more accurate the data delivered at the end of the analysis.

For the present invention, each column in the Doppler image buffer was derived from a 128 point power spectrum. Since the frequency filtering operation is very computational intensive (time consuming) reducing the amount of data reduces the time required to perform the filtering operation. Depending upon the current video mode, the image is either 376 (NTSC) or 448 (PAL) pixels high. A simple linear interpolation scheme is used to reduce this to 128 points.

(b) Perform a temporal smoothing on the power frequency spectrum.

Once the original power frequency spectrum is produced a temporal smoothing algorithm is applied. This in practice can be an optional step as the analysis outcome is rarely altered by the omission of this step.

(c) Determine the absolute value deviation for each frequency spectrum.

Next the system determined the absolute value deviation for each frequency spectrum. This is performed through the logic:

$$I = 0 \ldots X$$

$$MeanPow := \frac{\left(\sum_i Power_i\right)}{X}$$

$$AVD := \left(\frac{1}{X}\right) \cdot \left[\sum_i (|Power_i - MeanPow|)\right]$$

where AVD is the Absolute valuation deviation, $Power_i$ is the value of each frequency sample, MeanPow is the mean power for the entire sample set, and the height is the number of channels remaining after the compression. AVD is in essence the sum of the Power less the MeanPow from 1 to X where X is the number of channels being analyzed in a single doppler frame.

(d) Determine the mean power per frequency spectrum.

This is done by first summing the total power for the spectrum. Then, starting from one end of the spectrum, the power is progressively summed until one-half of the total power is exceeded. This point is used as the mean power per frequency spectrum.

(e) Apply one of a series of predetermined smoothing filters to each frequency column.

Figure 12:
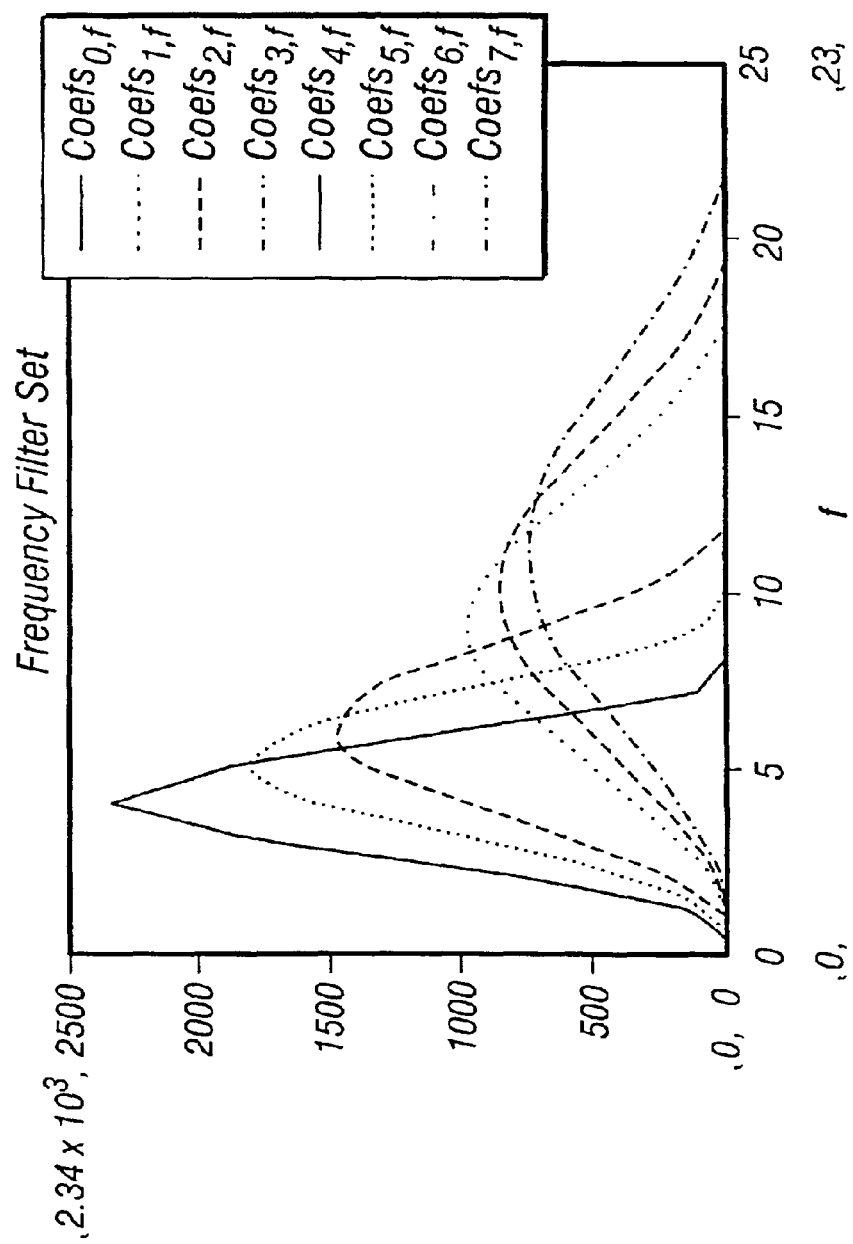
FIG. 12 illustrates the desired present filter characteristics.

Once the value of each frequency column is determined, a predetermined smoothing filter is applied to the frequency column. To reduce computational demand on the processor, the predetermined smoothing filters are stored in a memory available to the RISC processor. The AVD value helps determine which predetermined smoothing filter is applied to the particular frequency column. The number of predetermined smoothing filters is variable depending on the memory size, and the processor capacity dedicated to the feature of smoothing the frequency column. The predetermined smoothing filters form a filter library which may consist of any fixed number of filters. For the present invention, eight preset filters are used as shown in FIG. 12.

The filter length is found along the bottom axis and depending on the value of the AVD for a particular frequency column, the appropriate fixed smoothing filter is applied. In the current implementation, the filter is selected by multiplying the AVD by a constant factor (0.5) and then choosing the filter length closest to the result.

(f) Find the maximum value before the mean of each frequency spectrum;

Next is the determination of the Maximum Before the Mean (MBM) for each frequency spectrum. In the DD, working from the extreme point toward the baseline find the maximum value before the mean power point. This is called the Maximum Before the Mean (MBM).

(g) Establish a frequency spectrum threshold.

Normally the peak finding algorithm uses this MBM value multiplied by THRESHOLD_FACTOR (30/256) as it's threshold value. If MBM<=TRACE_THRESHOLD (24), then an alternate threshold is tried. The alternate threshold is maximum value of the power spectrum divided by two. If this maximum derived threshold is less than TRACE_THRESHOLD/2, the peak is set to be the baseline.

(h) Employ a peak finding algorithm.

The peak finding algorithm searches on the dominant side of the baseline working from the extreme point toward the baseline. The peak finding algorithm uses a point where the power spectrum value rises to cross the threshold. If the power spectrum is noisy the power may cross the threshold several times. In this noisy case, the area between the baseline or power spectrum and the threshold is accumulated for each section of the power spectrum which is below the threshold. The point where the power raises above the threshold with the largest area accumulated before it, is selected as the peak point.

(i) Apply a fixed width filter for temporal smoothing; and (j) Restoring the analyzed data to the proper image format The peak mean and max arrays need to be converted from the 128 point format to the display dimensions. This is done by finding the nearest corresponding display pixel. The following code is illustrative: out=((64+iTmp*rows)/128).

While the method described above provide particular values and descrete limitations on the process, it should be understood that the numbers are easily altered to handle a process using different fixed elements and libraries and does not depart from the scope of the present invention.

What is claimed is:

1. An ultrasound diagnostic instrument comprising:

a) a handheld module including a display, manual controls, and system circuitry for processing signals for display;

b) a transducer assembly coupled to the system circuitry for providing electrical signals from ultrasound waves for processing; and c) an electrocardiograph (ECG) module coupled to the handheld module by a cable and including leads for receiving ECG signals from a patient and ECG signal processing circuitry for applying ECG signals to the handheld module through the cable;

wherein said handheld module further comprises circuitry for performing spectral Doppler analysis and allowing for simultaneous ECG readings to be overlaid on a spectral Doppler display;

wherein the signal processing circuitry of the ECG module includes first amplification and filtering circuitry for signals from the leads and second amplification and filtering circuitry for processing signals from the first amplification and filtering circuitry for application to the handheld module, the first and second amplification and filtering circuitry being electrically isolated whereby a patient is electrically isolated from the handheld unit.

2. The ultrasound diagnostic instrument as defined by claim 1, wherein the ECG module receives control and power signals from the handheld module.

3. The ultrasound diagnostic instrument as defined by claim 1, wherein the first amplification and filtering circuit receives electrical power from the handheld module, the electrical power being capacitively coupled to the first amplification and filtering circuitry.

4. The ultrasound diagnostic instrument of claim 3, wherein the transducer assembly is coupled to the system circuitry through a cable.

5. The ultrasound diagnostic instrument as defined by claim 3, wherein the transducer assembly is integral with the handheld module.

6. The ultrasound diagnostic instrument as defined by claim 1, wherein, the first and second amplification and filtering circuitry are optically coupled.

7. The ultrasound instrument as defined by claim 1, wherein the first and second amplification and filtering circuitry are magnetically coupled.

8. The ultrasound instrument as defined by claim 1, wherein the first and second amplification and filtering circuitry are capacitively coupled.

9. The ultrasound diagnostic instrument as defined by claim 1, wherein the transducer assembly is coupled to the system circuitry through a cable.

10. The ultrasound diagnostic instrument as defined by claim 1, wherein the transducer assembly is integral with the handheld module.

11. A system for performing electrocardiography comprising:

a portable ultrasound device having a transducer, a beamformer, an image processor and one or more digital signal processors for signal filtering, detection and mapping;

a portable electrocardiogram monitor and having at least three electrical leads for measuring electrical potential across a person's chest, a differential amplifier for amplifying the measured electrical potential, a plurality of signal filters and gain amplifiers, and a means for electronically isolating the measured signal from other electrical inputs and interferences; and a portable display module for simultaneously displaying an image from said ultrasound device and signals from said electrocardiogram monitor;

wherein signal processing circuitry of the electrocardiogram monitor includes first amplification and filtering circuitry for signals from the leads and second amplification and filtering circuitry for processing signals from the first amplification and filtering circuitry for application to the ultrasound device, the first and second amplification and filtering circuitry being electrically isolated whereby a patient is electrically isolated from the ultrasound device.

12. The system of claim 11, wherein the electrocardiogram monitor receives control and power signals from the ultrasound device.

13. The system of claim 11, wherein the first and second amplification and filtering circuitry are optically coupled.

14. The system of claim 11, wherein the first and second amplification and filtering circuitry are magnetically coupled.

15. The ultrasound instrument as defined by claim 11, wherein the first and second amplification and filtering circuitry are capacitively coupled.

* * * * *